Figure 1:
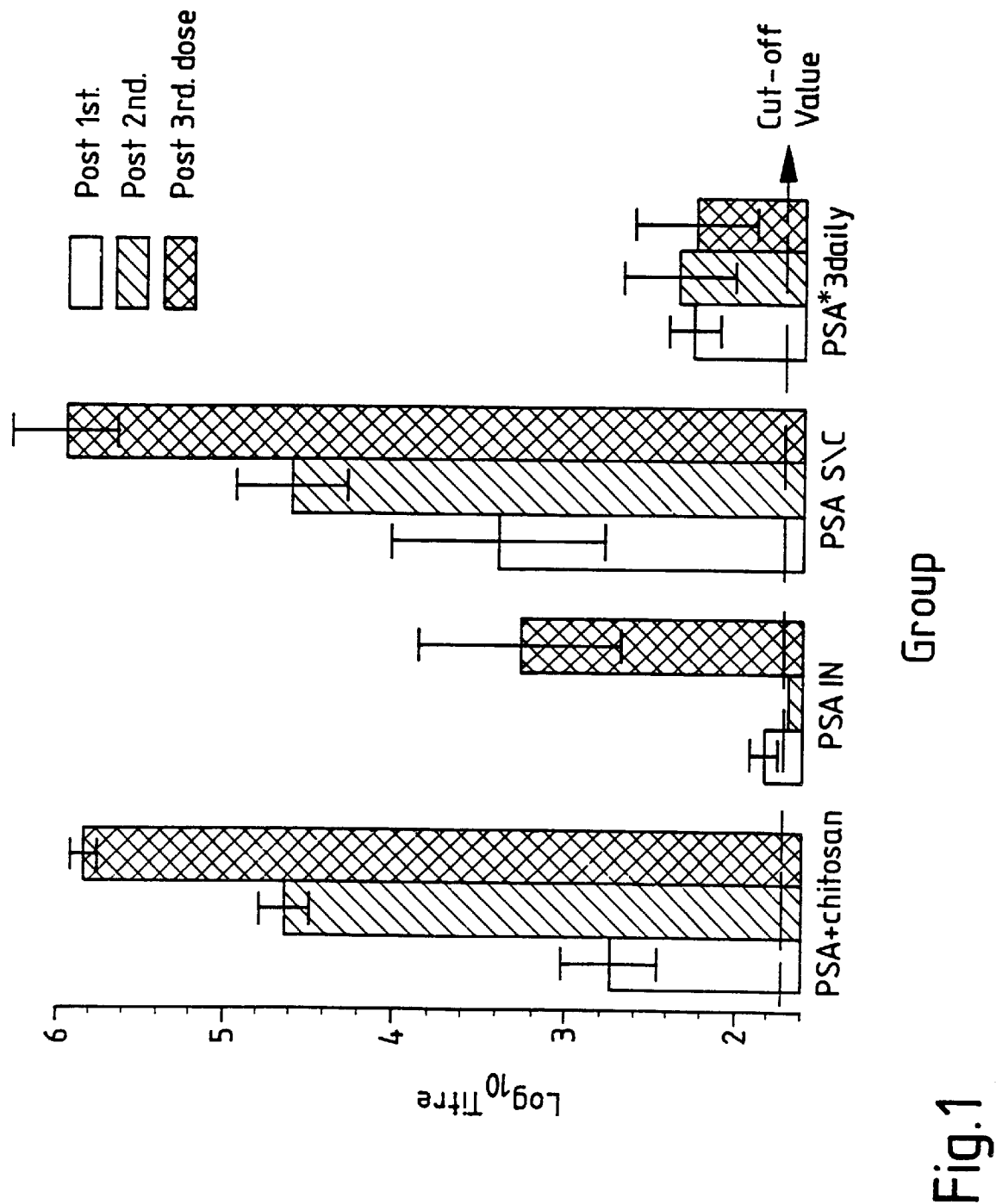

United States Patent [19]

Chatfield

[11] Patent Number: 6,048,536
[45] Date of Patent: Apr. 11, 2000

[54] VACCINE COMPOSITIONS

[75] Inventor: Steven Neville Chatfield, London, United Kingdom

[73] Assignee: Medeva Holdings BV, Amsterdam, Netherlands

[21] Appl. No.: 08/817,417

[22] PCT Filed: Sep. 21, 1995

[86] PCT No.: PCT/GB95/02231

§ 371 Date: Apr. 2, 1997

§ 102(e) Date: Apr. 2, 1997

[87] PCT Pub. No.: WO96/10421

PCT Pub. Date: Apr. 11, 1996

[30] Foreign Application Priority Data

Oct. 4, 1994 [GB] United Kingdom ............... 9419979

[51] Int. Cl.⁷ .............. A61K 39/145; A61K 39/12; A61K 45/00; A01N 43/04
[52] U.S. Cl. .................. 424/206.1; 424/193.1; 424/199.1; 424/196.11; 424/204.1; 424/210.1; 424/278.1; 424/279.1; 435/206.1; 514/55
[58] Field of Search ............... 424/199.1, 193.1, 424/196.11, 204.1, 206.1, 210.1, 278.1, 279.1; 435/206; 514/55

[56] References Cited

U.S. PATENT DOCUMENTS

| | | | |
|---|---|---|---|
| 4,659,569 | 4/1987 | Mitsuhashi et al. | 424/89 |
| 5,629,011 | 5/1997 | Illum | 424/434 |

FOREIGN PATENT DOCUMENTS

| | | |
|---|---|---|
| 0183556A2 | 11/1985 | European Pat. Off. . |
| 0506326A3 | 3/1992 | European Pat. Off. . |
| 5163161 | 6/1993 | Japan . |
| 6166635 | 6/1994 | Japan . |
| WO 90/09780 | 9/1990 | WIPO . |
| 97/20576 | 6/1997 | WIPO .............. A61K 39/39 |

OTHER PUBLICATIONS

Nishimura et al. Jun. 1987 Vaccine vol. 5 pp. 136–140.
Renfry et al., "Morphological and biochemical characterization of influenza vaccines commercially available in the United Kingdom", Vaccine 1994, vol. 12, No. 8, pp. 747–752.
Iida et al., "Stimulation of non–specific host resistance against Sendai virus and *Escherichia coli* infections by chitin derivatives in mice", Vaccine Dec. 1987, vol. 5, pp. 270–273.
Nishimura et al., "Immunological activity of chitin and its derivatives", Vaccine Mar. 1984, vol. 2., pp. 93–99.
Biol. Nauki (Byelarus) 1992, (4) pp. 87–89 (Abstract only supplied).
de Haan et al., "Mucosal immunoadjuvant activity of liposomes: induction of systemic IgG and secretory IgA responses in mice by intranasal immunization with an influenza subunit vacccine and coadministered liposomes," *Vaccine* 13, pp. 155–162 (1995).
Oka et al., "Enhancing effects of pertussis toxin B oligomer on the immunogenicity of influenza vaccine administered intranasally," *Vaccine* 12, pp. 1255–1258 (1994).
Nishimura et al., "Adjuvant activity of chitin derivatives in mice and guinea–pigs," *Vaccine 3*, pp. 379–384 (1985).

*Primary Examiner*—Anthony C. Caputa
*Assistant Examiner*—Mary K Zeman
*Attorney, Agent, or Firm*—Heslin & Rothenberg, P.C.

[57] ABSTRACT

The invention relates to a vaccine composition adapted for mucosal administration, and in particular for intranasal administration, the composition comprising an influenza virus antigen or antigens, such as haemagglutinin and neuraminidase influenza virus antigens, and an effective adjuvant amount of a chitosan. The compositions can be used to immunise a host against infection with influenza, the chitosan serving to enhance the stimulation of a protective IgA mucosal immune response and an IgG systemic immune response.

19 Claims, 4 Drawing Sheets

VACCINE COMPOSITIONS

The invention relates to a vaccine composition for intranasal administration comprising influenza virus antigens and a mucosal adjuvant. The invention also relates to a method of immunising a patient against influenza by administering the said composition to the patient, and a method of enhancing the immunogenicity of an influenza viral antigen when administered intranasally, by co-administering therewith the said adjuvant. In a further aspect, the invention provides the use of an influenza viral antigen in combination with a chitosan for the manufacture of a vaccine composition for intranasal administration to immunise a patient against influenza.

Current influenza vaccines consist of either inactivated whole virus, disrupted virus (split vaccines) or purified preparations of the membrane glycoproteins haemagglutinin (HA) and neuraminidase (NA) sub-unit vaccines. Haemagglutinin and neuraminidase are the antigens to which protective antibody responses are directed, haemagglutinin being the major protective antigen. Estimates of the efficacy of these parenterally administered vaccines vary greatly. Such vaccines are believed to act primarily by eliciting circulating anti-haemagglutinin IgG antibodies that transudate into the lower respiratory tract.

M. L. Clements et al, J. Clinical Microbiology 24, 157–160, 1986, have previously reported that both secretory IgA and serum IgG participate in immunity to influenza virus. Moreover, in mice, a number of published studies have demonstrated the importance of respiratory IgA to protection against influenza infection. It has also been found that an advantage of stimulating a local IgA response to influenza is that it is often of a broader specificity than the serum response and thus can provide cross-protection against viruses possessing haemagglutinin molecules different from those present in the vaccine. Accordingly, influenza vaccines that elicit both local secretory and serum anti-haemagglutinin responses should provide superior immunity to current vaccines. However, parenteral vaccination (intramuscular, sub-cutaneous etc) is not effective at eliciting local antibody production, if there has been no previous mucosal exposure (e.g. infection). In order to stimulate the mucosal immune system, the vaccine must be applied topically to a mucosal surface.

Mucosal administration of influenza vaccine would have a number of advantages over traditional parenteral immunisation regimes. Paramount amongst these are more effective stimulation of the local mucosal immune system of the respiratory tract and the likelihood that vaccine uptake rates would be increased because the fear and discomfort associated with injections would be avoided. Accordingly, a number of attempts have been made to develop mucosal influenza vaccines. A drawback however is that inactivated vaccines are often poorly immunogenic when given mucosally. In order to overcome this problem, different approaches to improving the immunogenicity of flu vaccines given orally or intranasally have included the use of the B sub-unit of cholera toxin (CTB) as an adjuvant, encapsulation of the vaccine in a variety of microspheres, and the use of live attenuated strains. To date however no practical means of enhancing the immunogenicity of mucosally administered flu vaccines has been developed.

It has now been found by the Applicant that by administering the haemagglutinin and neuraminidase antigens of influenza together with a particular chitosan derivative in an intranasal formulation, it is possible to achieve good IgG and good IgA responses.

Chitosans are derivatives of chitin or poly-N-acetyl-D-glucosamine in which the greater proportion of the N-acetyl groups have been removed through hydrolysis.

Chitosans have previously been used in pharmaceutical formulations and are disclosed in EP-A-0460020 as mucosal absorption enhancers, However, EP-A-0460020 does not disclose or suggest that the chitosan could provide an adjuvant effect when administered in a vaccine composition.

The present Applicant have now found that if a chitosan is incorporated into intranasal vaccine compositions containing the neuraminidase and haemagglutinin antigens of influenza virus, good systemic and local immune responses are produced.

Accordingly, in a first aspect the invention provides a vaccine composition adapted for mucosal administration; the composition comprising an influenza virus antigen(s); and an effective adjuvant amount of chitosan.

The vaccine composition is preferably adapted for intra nasal administration.

Preferably the composition contains both haemagglutinin and neuraminidase influenza virus antigens.

In a preferred embodiment the invention provides a vaccine composition adapted for intranasal administration; the composition comprising purified haemagglutinin and neuraminidase influenza virus antigens; and an effective adjuvant amount of a chitosan.

It is preferred that the purified haemagglutinin and neuraminidase antigens are present in the form of rosettes. The rosettes preferably are particles with a radius in the range 10 to 25 nanometers.

It is preferred that the rosettes are substantially free of lipid and, moreover, it is preferred that the purified haemagglutinin and neuraminidase antigens preparation as a whole is substantially free of lipids.

An example of a haemagglutinin/neuraminidase preparation suitable for use in the compositions of the present invention is the "Fluvirin" product manufactured and sold by Evans Medical Limited of Speke, Merseyside, United Kingdom, and see also S. Renfrey and A. Watts, Vaccine, 1994, Volume 12, Number 8, pp 747–752.

The compositions can contain influenza virus antigens from a single viral strain, or from a plurality of strains. For example, the composition can contain antigens taken from up to three or more viral strains. Purely by way of example the composition can contain antigens from one or more strains of influenza A together with antigens from one or more strains of influenza B.

Preferably the chitosan is water-soluble.

The chitosan may advantageously be a deacetylated chitin which is at least 80% deacetylated.

Preferably the chitosan is at least 85% de-acetylated, and more preferably is 88% to 90% de-acetylated.

A particular de-acetylated chitosan is the "Sea Cure +" chitosan glutamate available from Protan Biopolymer A/S, Drammen, Norway.

In a further aspect, the invention provides a method of immunising a host against infection with influenza, which method comprises administering to a mucosal surface of the host (preferably intranasally) a vaccine composition comprising influenza virus antigens such as purified haemagglutinin and neuraminidase antigens together with an effective adjuvant amount of a chitosan as hereinbefore defined.

In a further aspect, the invention provides a method of enhancing a protective IgA mucosal immune response and an IgG systemic immune response by administering (preferably intranasally) to a mucosal surface of the patient a vaccine composition comprising influenza virus antigens such as purified haemagglutinin and neuraminidase; and an effective adjuvant amount of a chitosan as hereinbefore defined.

In a still further aspect, the invention provides a method of enhancing the immune response of influenza virus antigens such as purified haemagglutinin and neuraminidase, (e.g. when administered intranasally), by co-administering therewith a chitosan as hereinbefore defined.

The compositions of the invention, and in particular intranasal compositions, can be formulated as liquids or dry powders, for administration as aerosols or drops.

Compositions for administration as nasal drops may contain one or more excipients of the type usually included in such compositions, for example preservatives, viscosity adjusting agents, tonicity adjusting agents, buffering agents and the like.

In order to ensure that the chitosan remains soluble in the aqueous medium, and to ensure also that the haemagglutinin is not adversely affected by too acidic a pH, a solution (e.g. for intranasal administration) preferably has a pH in the range 5.5 to 6.5, most preferably approximately pH6.

The present invention also contemplates the provision of means for dispensing intranasal formulations of influenza virus antigens such as purified surface antigen, and chitosan. A dispensing device may, for example, take the form of an aerosol delivery system, and may be arranged to dispense only a single dose, or a multiplicity of doses.

The vaccine will be administered to the patient in an amount effective to stimulate a protective immune response in the patient. For example, the vaccine may be administered to humans in one or more doses, each dose containing 1–250 microgrammes and more preferably 5–50 microgrammes of protein prepared from each virus strain. For example, where haemagglutinin and neuraminidase preparations are prepared from three virus strains, e.g. 2× Influenza A and 1× Influenza B, a total dose of viral protein administered could be in the range 15–150 microgrammes.

BRIEF DESCRIPTION OF THE FIGURES

FIG. 1 illustrates the serum IgG anti-haemagglutinin response in mice immunised with PSA. Each bar represents the geometric mean titre of four mice. The error bars represent 1 standard error of the mean. The cut-off value is 50 which is the lower limit of detection.

FIG. 2 illustrates the nasal IgA anti-haemagglutinin response in mice immunised with purified surface antigen (PSA). As with FIG. 1, each bar represents the geometric mean titre of four mice, and the error bars represent 1 standard error of mean.

FIGS. 3 and 4 illustrate the determination of nasal and pulmonary anti-haemagglutinin secreting cells of mice immunised with purified surface antigen, using ELISPOT. FIG. 3 uses a log scale whilst FIG. 4 uses a linear scale.

EXAMPLE 1

Preparation of influenza B purified surface antigen/chitosan glutamate formulation 1A. A solution of 1% chitosan glutamate, a medium viscosity de-acetylated chitin having approximately 11% residual N-acetyl groups, was prepared by dissolving the chitosan glutamate in 0.8% sodium chloride. The grade of chitosan glutamate used was "Sea Cure +210", available from Protan Biopolymer A/S, Drammen, Norway.

1B. Influenza purified surface antigen (PSA) containing both Influenza A and Influenza B protein, commercially available from Evans Medical Limited, Speke, Merseyside, United Kingdom, under the Trade Mark "Fluvirin", was made up in phosphate buffered saline to give a protein concentration of approximately 1 mg/ml. The PSA consists almost entirely of the spike protein haemagglutinin (HA), although it does contain some neuraminidase.

1C. A 1:1 mixture of the chitosan glutamate solution and the PSA solution was prepared to give an intranasal vaccine composition containing 0.5% chitosan glutamate (11% acetylated), 0.8% NaCl, 0.1% PSA and phosphate buffer to give a solution pH of 6.

1D. Control solutions containing the same concentrations of PSA but not chitosan glutamate, and the same concentrations of chitosan glutamate but no PSA, were also prepared. In addition, a composition comprising the same concentration of PSA adsorbed on to the known adjuvant alhydrogel (aluminium hydroxide) was prepared. The PSA was adsorbed on to the alhydrogel overnight at 4° C.

EXAMPLE 2

Mice Immunisation Studies

2A. The four compositions prepared as described in Example 1 were administered to groups of twelve adult (6–8 weeks) female BALB/c mice as follows:

Group 1. 20 μl (10 μl per nostril) PSA/chitosan solution administered intranasally. PSA dose=10 μg.

Group 2. 20 μl PSA administered intranasally (total PSA dose=10 μg).

Group 3. 200 μl PSA/alhydrogel administered subcutaneously (PSA dose=10 μg).

Group 4. 20 μl chitosan solution administered intranasally.

Group 5. 20 μl PSA (10 μl per nostril) administered daily for three days. (Groups of four mice employed for this study).

2B. The immunisation procedure was carried out three times at monthly intervals, with the exception of Group 5 where the mice were immunised with three successive daily doses. The immunisation and sampling regime is shown in Table 1.

Immunisation and sampling regime

TABLE 1

| Immunisation | Day | Sample | Day |
|---|---|---|---|
| 1 | 1 | 1 | 21 |
| 2 | 30 | 2 | 44 |
| 3 | 57 | 3 | 71 + 72 |

At each sampling point four mice from each group were terminally bled by cardiac puncture, their heads were removed and their nasal passages lavaged with 1 ml PBS +1% bovine serum albumin. Group 5 contained four mice only so blood was obtained by tail puncture for the first two samples and nasal washes were only performed at the third sampling point.

Antibody assays

In all assays whole influenza vaccine (WIV) was used as antigen. Although WIV is only ~50% HA the assays were thought to be measuring primarily anti-HA antibodies. This assumption was confirmed by substituting PSA (~100% HA) for WIV and repeating some assays. The results were similar with either antigen. HA-specific serum IgG and nasal IgA antibodies were measured by Enzyme Linked Immunosorbant Assay (ELISA). After correcting for background, the individual optical density (OD) dilution curves were plotted and the titre values determined. The titre was determined as the dilution of serum that gave an OD reading of 0.2 or the dilution of nasal wash that gave an OD reading of 0.1.

As well as taking nasal washes at the third sample lymphocytes were isolated from the mucous membranes of the nasal cavity and the lungs and the local immune response analysed by ELISPOT.

Results

1. Serum anti-HA serum response

Purified Surface Antigen (FIG. 1 and Table 2)

As expected a good serum response was elicited by subcutaneous (S\C) immunisation with PSA + Alhydrogel. All the animals tested had seroconverted after the primary immunisation and the geometric mean titre (GMT) was good. The response increased after each boost, the GMT after the third dose was very high (~800,000). In contrast the serum response to PSA alone administered intranasally was poor: only two of four mice had seroconverted after the first dose, none of the mice tested had serum HA antibodies after the second dose (these are separate mice from those tested after the first immunisation) and although all animals tested had seroconverted after the third dose the GMT was lower than that of animals receiving one dose of PSA + Alhydrogel. Chitosan enhanced the serum response of intranasally administered PSA; after the third vaccination the antibody response in mice that received PSA + chitosan was 360-fold greater than that of mice receiving PSA alone I\N. The magnitude of the serum response in the PSA + chitosan mice was very similar to that of S\C immunised mice; in fact there was no statistical difference in the GMT's of the two groups at any sampling point (Students t-Test p>0.01).

Some mice were immunised three times on successive days with PSA alone administered intranasally to study whether this regime had advantages over the once monthly regime. Although all the mice in this group had detectable serum antibodies 21 days after the first dose and the GMT at this time point was greater than in mice that had received a single dose of PSA intranasally, the number of mice seropositive decreased during the course of the study although the GMT did not (in this group the same mice were sampled at each time point). At the final time point the GMT of the mice on the monthly regime was an order of magnitude greater than mice on the daily regime.

TABLE 2

Serum IgG anti-HA response in PSA immunised mice

| Group | Post-Dose 1 | | Post-Dose 2 | | Post-Dose 3 | |
| --- | --- | --- | --- | --- | --- | --- |
|  | Seroconversion | GMT | Seroconversion | GMT | Seroconversion | GMT |
| PSA + Chitosan | 4/4 | 557 | 4/4 | 40504 | 4/4 | 653113 |
| PSA I/N | 2/4 | 67 | 0/4 | <50 | 4/4 | 1818 |
| PSA S/C | 4/4 | 2339 | 4/4 | 35196 | 4/4 | 816552 |
| PSA 3 daily doses | 4/4 | 182 | 3/4 | 229 | 2/4 | 180 |

[a]No. positive/No. tested
[b]Geometric Mean Titre

2. Nasal wash IgA anti-HA response

Figure 2:
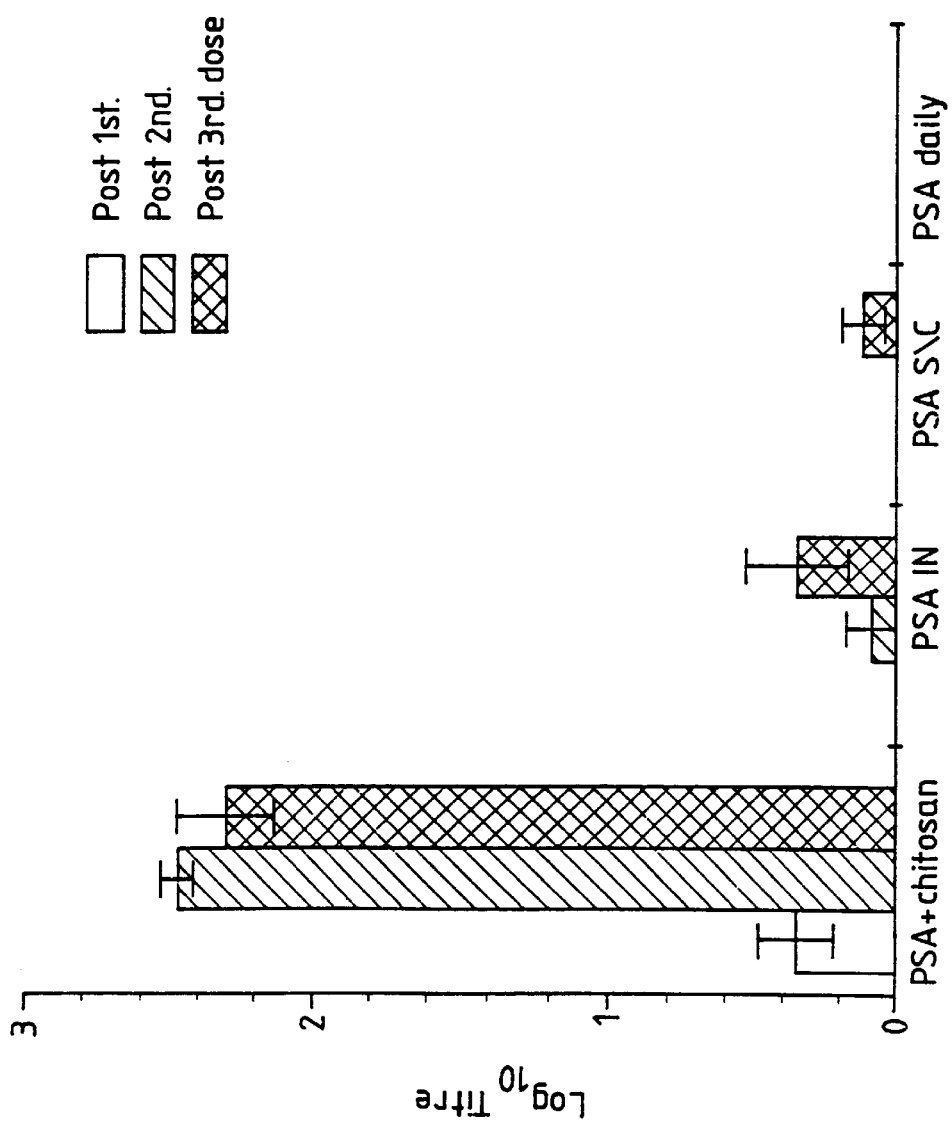

Purified Surface Antigen (FIG. 2 and Table 3)

PSA + Alhydrogel given subcutaneously was very poor at inducing a nasal IgA response which is consistent with our previous findings and those of others. PSA alone given intranasally was also a poor mucosal immunogen although it was slightly better than subcutaneous immunisation in terms of the number of animals responding. Adding chitosan greatly boosted the IgA response, although the response was low after the first dose, HA-specific IgA could be detected in three out of four mice. The IgA response was boosted greatly in these mice by the second immunisation. The final immunisation had little effect; in fact the mean specific IgA levels had decreased slightly.

TABLE 3

Nasal IgA anti-HA response in PSA immunised mice

| Group | Post-Dose 1 | | Post-Dose 2 | | Post-Dose 3 | |
| --- | --- | --- | --- | --- | --- | --- |
|  | Mucosal-conversion | GMT | Mucosal-conversion | GMT | Mucosal-conversion | GMT |
| PSA + Chitosan | 3/4 | 2.26 | 4/4 | 282.81 | 4/4 | 184.47 |
| PSA I/N | 0/4 | <1 | 1/4 | 1.20 | 3/4 | 2.31 |
| PSA S/C | 0/4 | <1 | 0/4 | <1 | 2/4 | 1.32 |
| PSA 3 daily doses |  |  |  |  | 0/4 | <1 |

[a]No. positive\No. tested
[b]Geometric Mean Titre

Responses to Chitosan Alone

The sera and nasal lavage fluid from the control mice immunised with chitosan alone were negative in all the assays.

Figure 3:
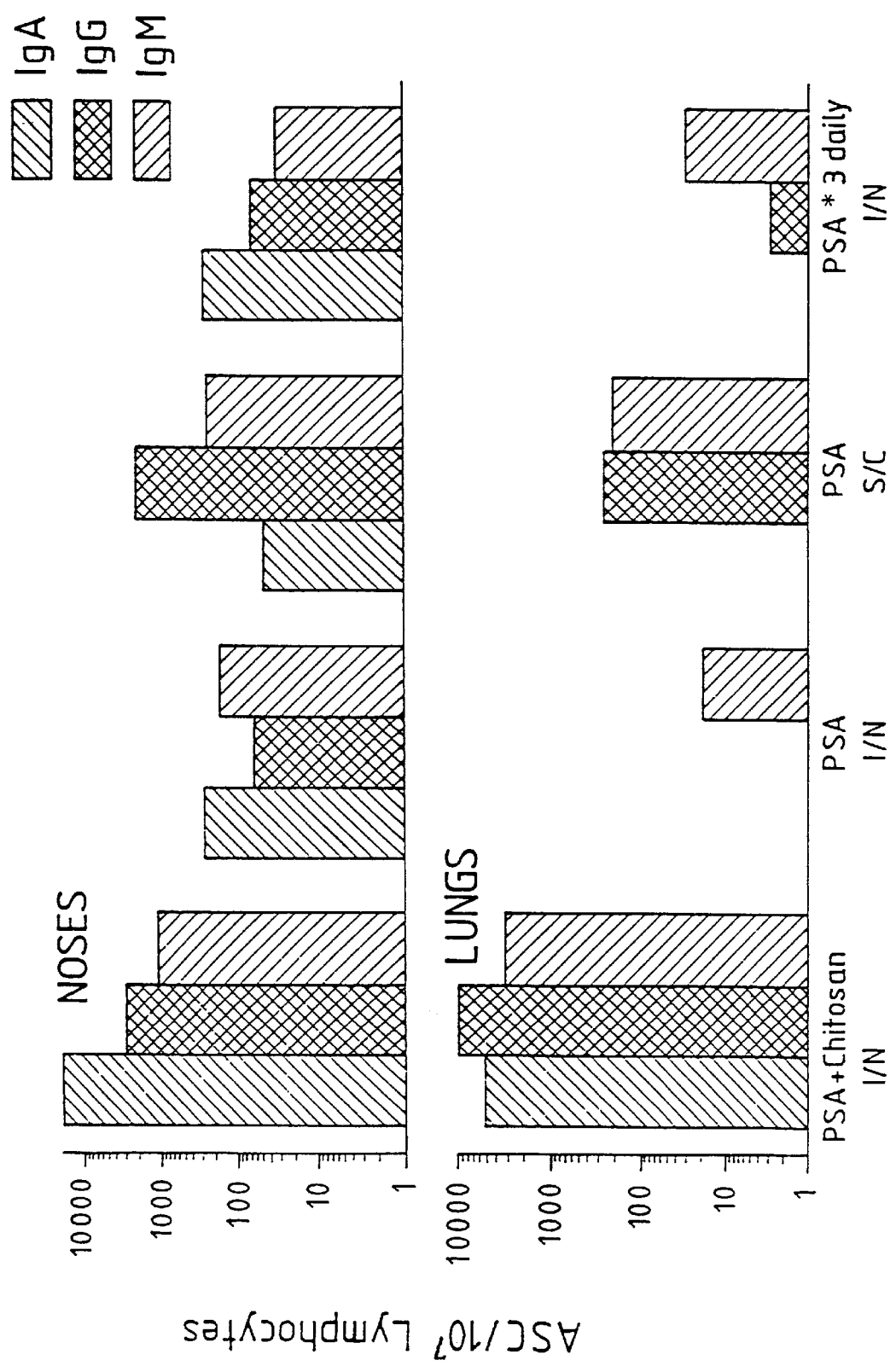

Local anti-HA antibody secreting cell response (ASC) in nasal and pulmonary tissues Lymphocytes were isolated from the nasal mucosa and lung parenchyma of groups of four mice at the third sampling point. Lymphocytes from individual mice were pooled and assayed for cells secreting IgA, IgG and IgM anti-flu antibodies using ELISPOT. The results are shown in FIGS. 3a and 3b.

B cells secreting HA-specific antibodies were detectable in the nasal and lung tissue of all groups. There were far greater number of such cells in the PSA + chitosan group and this is most apparent when the results are plotted on a linear scale (FIG. 3b). In all cases, except subcutaneously immunised mice, IgA antibody secreting cells (ASC) predominated in the nasal cavity whereas either IgG or IgM predominated in the lungs. The magnitude of the response is similar in the lungs and nose of PSA + chitosan mice.

The aforementioned examples are merely exemplary of the present invention and are not intended in any way to limit the scope of the invention which is defined solely by the claims appended hereto.

I claim:

1. A pharmaceutical product comprising a dispensing device adapted to deliver a composition intranasally, in combination with a composition adapted for mucosal administration; the composition comprising an influenza virus antigen and an effective adjuvant amount of a chitosan, the chitosan being a deacetylated chitin which is at least 80% deacetylated.

2. A pharmaceutical product according to claim 1 wherein the dispensing device is an aerosol delivery system.

3. A pharmaceutical product according to claim 2 wherein the chitosan is at least 85% deacetylated.

4. A pharmaceutical product according to claim 3 wherein the chitosan is 88% to 90% deacetylated.

5. A pharmaceutical product according to claim 1 wherein the influenza virus antigen comprises haemagglutinin and neuraminidase influenza virus antigens.

6. A method of immunising a host against infection with influenza virus which comprises administering to a mucosal surface of the host, a composition comprising an influenza virus antigen and an effective adjuvant amount of a chitosan, the chitosan being a deacetylated chitin which is at least 80% deacetylated.

7. A method according to claim 6 wherein the chitosan is at least 85% deacetylated.

8. A method according to claim 7 wherein the chitosan is 88% to 90% deacetylated.

9. A method according to claim 6 wherein the composition is administered intranasally.

10. A method according to claim 6 wherein the influenza virus antigen comprises haemagglutinin and neuraminidase influenza virus antigens.

11. A method of enhancing a protective IgA mucosal immune response and an IgG systemic immune response in a patient that comprises administering to a mucosal surface of the patient a composition comprising an influenza virus antigen and an effective adjuvant amount of a chitosan, the chitosan being a deacetylated chitin which is at least 80% deacetylated.

12. A method according to claim 11 wherein the chitosan is at least 85% deacetylated.

13. A method according to claim 12 wherein the chitosan is 88% to 90% deacetylated.

14. A method according to claim 11 wherein the composition is administered intranasally.

15. A method according to claim 11 wherein the influenza virus antigen comprises haemagglutinin and neuraminidase influenza virus antigens.

16. A method of enhancing an immune response to an intranasal administration of an influenza virus antigen which comprises concurrent intranasal administration of an influenza virus antigen and an effective immune response-enhancing amount of a chitosan, the chitosan being a deacetylated chitin which is at least 80% deacetylated.

17. A method according to claim 16 wherein the chitosan is at least 85% deacetylated.

18. A method according to claim 17 wherein the chitosan is 88% to 90% deacetylated.

19. A method according to claim 16 wherein the influenza virus antigen comprises haemagglutinin and neuraminidase influenza virus antigens.

* * * * *

UNITED STATES PATENT AND TRADEMARK OFFICE
CERTIFICATE OF CORRECTION

PATENT NO.    : 6,048,536
DATED         : April 11, 2000
INVENTOR(S)   : Steven Neville Chatfield It is certified that error appears in the above-identified patent and that said Letters Patent is hereby corrected as shown below:

Col. 6, line 31, delete "3a and 3b" and replace with --3 and 4--.

Figure 4:
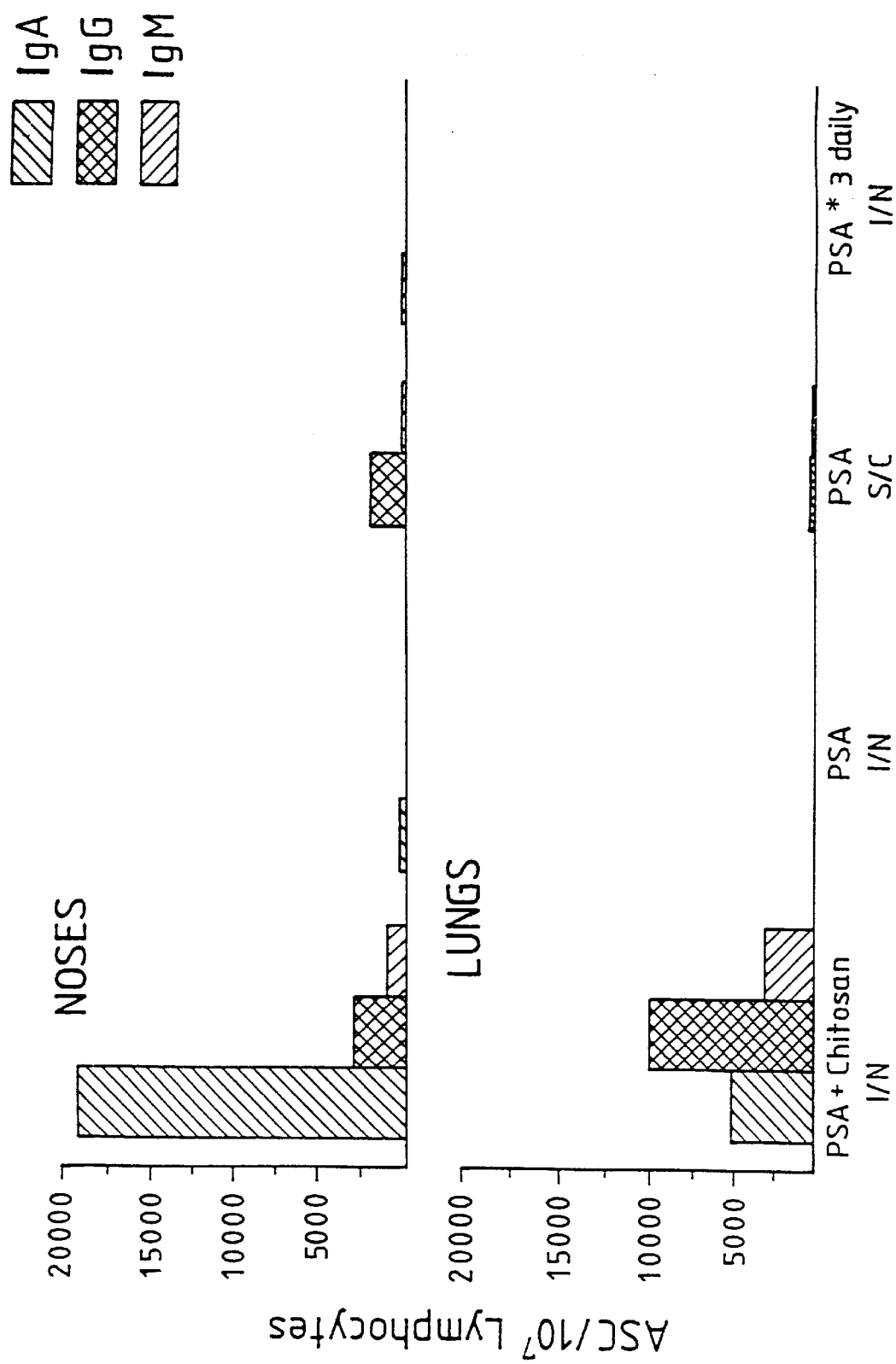

Col. 6, line 36, delete "(FIG. 3b)" and replace with --(FIG. 4)--.

Signed and Sealed this

Twentieth Day of March, 2001

Attest:

NICHOLAS P. GODICI

*Attesting Officer*   *Acting Director of the United States Patent and Trademark Office*

UNITED STATES PATENT AND TRADEMARK OFFICE
Certificate

Patent No. 6,048,536

Patented: April 11, 2000

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Steven Neville Chatfield, London, UK; and Lisbeth Illum, Nottingham, UK.

Signed and Sealed this Fifteenth Day of April 2003.

MICHAEL P. WOODWARD
*Supervisory Patent Examiner*
Art Unit 1631